United States Patent [19]

Mück et al.

[11] Patent Number: 4,703,129
[45] Date of Patent: Oct. 27, 1987

[54] PROCESS FOR THE CONTINUOUS PREPARATION OF TRIOXANE

[75] Inventors: Karl-Friedrich Mück; Karlheinz Burg, both of Wiesbaden, Fed. Rep. of Germany

[73] Assignee: Hoechst Aktiengesellschaft, Frankfurt am Main, Fed. Rep. of Germany

[21] Appl. No.: 808,846

[22] Filed: Dec. 13, 1985

[30] Foreign Application Priority Data

Dec. 17, 1984 [DE] Fed. Rep. of Germany ....... 3445921

[51] Int. Cl.$^4$ .................. C07D 323/06; C07D 319/06; C07D 317/12
[52] U.S. Cl. .................................. 549/368; 549/369; 549/347; 549/430
[58] Field of Search ........................................ 549/368

[56] References Cited

FOREIGN PATENT DOCUMENTS 0012304 2/1982 European Pat. Off. .
0017067 9/1982 European Pat. Off. .
1135491 8/1965 Fed. Rep. of Germany .
1012372 12/1965 United Kingdom .

Primary Examiner—Norma S. Milestone
Attorney, Agent, or Firm—Connolly & Hutz

[57] ABSTRACT

The invention relates to a process for the continuous preparation of trioxane, optionally together with cyclic formals, from an aqueous formaldehyde solution in the presence of acidic solid-bed catalysts, the reaction taking place without simultaneous evaporation.

The process according to the invention can be carried out even at high formaldehyde concentrations without appreciable paraformaldehyde deposits.

9 Claims, No Drawings

PROCESS FOR THE CONTINUOUS PREPARATION OF TRIOXANE

The preparation of trioxane from aqueous formaldehyde solutions has been described several times in the literature (cf. Walker, Formaldehyde, Reinhold Publ., New York, 3rd edition (1964), pages 198–199). In these cases aqueous formaldehyde solutions are converted at fairly high temperatures using acidic catalysts and the trioxane is removed from the reaction chamber by distillation. In addition to acids, ion exchangers are also recommended in the literature as catalyts (cf. German Patent No. 1,135,491). The synthesis vapor, which, in addition to trioxane, water and formaldehyde, also contains by-products of the synthesis, is under these circumstances continuously removed from the reaction mixture. This takes place by rectification, usually in a concentration column mounted on the reactor as specified in U.S. Pat. No. 2,304,080 or in a column with concentrating and stripping section as specified in British Patent No. 1,012,372. The trioxane-rich phase obtained is then worked up by extraction and/or any other known separation process.

Although when ion exchangers are used as catalysts the formation of by-products—in comparison to the use of acids—is reduced, ion exchangers can only be used without difficulty in the procedures hitherto known if the concentration of the formaldehyde solution is not more than approx. 40% by weight. With higher formaldehyde concentrations, on the other hand, paraformaldehyde deposits are increasingly encountered in the reaction reactor so that even at a formaldehyde concentration of approx. 60% by weight a continuous carrying out of the process over a prolonged period is no longer possible. With low formaldehyde concentrations, on the other hand, the achievable trioxane equilibrium concentrations are so small that such a process is not economical.

Moreover, in conventional circulation reactors ion exchangers are found not to have sufficient mechanical stability to guarantee long reactor running times.

Even according to the processes in European Patent Nos. 0,012,304 and 0,017,067 the quantity of by-products, particularly formic acid and paraformaldehyde, is very considerable.

The object of the invention was therefore to provide a process for the continuous preparation of trioxane, optionally together with cyclic formals, in which the disadvantages described of the prior art are at least substantially avoided.

According to the invention this is achieved by a procedure in which the conversion is carried out without simultaneous evaporation.

The present invention therefore relates to a process for the continuous preparation of trioxane, optionally together with cyclic formals, by trimerization of formaldehyde in aqueous solution which optionally contains in addition at least one diol and/or at least one epoxide, in the presence of acidic solid bed catalysts wherein the conversion is carried out without simultaneous evaporation.

In a surprising manner, by the process according to the invention even highly concentrated formaldehyde solutions which may contain up to 80% by weight of formaldehyde can be made to react without appreciable paraformaldehyde deposits being encountered. The formation of by-products such as formic acid, methylformate, methylal, trioxepan, tetroxane and the like is in addition very small. The trioxane contents correspond to the equilibrium value. The catalysts used according to the invention are, in addition, stable over a prolonged period under the experimental conditions according to the invention.

According to the invention, the trimerization reaction of formaldehyde to form trioxane is carried out without simultaneous evaporation, i.e. without removal in particular of trioxane and optionally of cyclic formals from the reaction system. The residence time of the reaction mixture in the reactor is, according to the invention, very short and, depending on the reaction temperature, is in general at least 0.1 minute, expediently between 0.1 and 15 minutes, preferably between 0.9 and 9 minutes and particularly preferably between 2 and 5 minutes. In this connection higher reaction temperatures naturally result in shorter residence times.

The formaldehyde content in the feed solution may be about 30 to about 80% by weight; the process according to the invention exhibits its particular advantages in the concentration range from about 60 to about 80% by weight.

The temperatures at which the conversion takes place are, depending on pressure, expediently between 80° to 140° C., temperatures of 90° to 120° C. being preferred. The pressure in the reactor which in general is 0.5 to 10 bar, preferably 1 to 5 bar, is, like the temperature, not critical per se; it should, however, always be chosen so that no evaporation takes place in the reactor.

In accordance with the invention the known acidic solids, whose acid strength must be sufficiently high to guarantee an adequate catalysis of the trimerization reaction, are suitable as catalysts. This is, for example, the case for solids containing sulfonic acid groups. Suitable acidic solid catalysts of this type for the purposes according to the invention are, for example, described in German Auslegeschrift No. 1,135,491, U.S. Pat. No. 3,176,023, British Patent No. 1,012,372, and in German Auslegeschriften Nos. 1,543,340 and 2,001,070. Here the following may be mentioned as acidic solid catalysts by way of example: cation exchangers containing sulfonic acid groups, zeolites, so-called solid "super acids" i.e. solids based on water-containing metal oxides such as iron(III) oxide, zirconium dioxide or titanium dioxide which are impregnated with sulfuric acid and subsequently calcined at fairly high temperatures. In this connection the cation exchangers containing sulfonic acid groups, in particular those based on crosslinked polystyrene or fluoropolymers, are preferred. The cation exchangers may have a macroporous or gel structure, the latter being preferred.

The exchange capacity of these cation exchangers is in general between 0.5 and 5 eq/liter of swollen substance, preferably between 0.7 and 2.5 eq/liter.

If a mixture of trioxane and at least one cyclic formal is to be prepared by the variant according to the invention, 1 to 25%, preferably 2 to 15%, referred to formaldehyde of at least one diol and/or at least one epoxide are expediently added to the aqueous formaldehyde solution. The diols suitable for this purpose are in particular 1,2-diols, 1,3-diols and α,ω-diols. Likewise, instead of the 1,2-diols the corresponding epoxides or mixtures of the two can also be used. Ethylene glycol, ethylene oxide, 1,2-propylene glycol; propylene oxide, 1,3-propylene glycol, 1,2-butanediol, 1,3-butanediol, 1,4-butanediol and 3-butene-1,2-diol have, for example, proved suitable. In this connection, according to the invention, ethylene glycol, ethylene oxide, 1,2-propylene glycol and 1,4-butanediol are preferably used, and particularly preferably ethylene glycol and ethylene oxide.

According to the invention the reaction is carried out in a reactor which is preferably constructed as a tubular reactor (flow tube). Tubular reactors of this type are described in their essential construction in Ullmann, Encyklopädie der technischen Chemie (Encyclopedia of Industrial Chemistry), Verlag Chemie, 4th edition, 1973, vol. 3, pages 350–352. The reactor can moreover be constructed as a bundle of tubes. Expediently, the reactor also has a preheating zone.

The reaction mixture leaving the reactor contains quantities of trioxane which correspond to the equilibrium value. The formic acid content, referred to the trioxane produced, is usually less than 1.5%. The reaction mixture is then subjected to an enrichment of the trioxane and optionally of the cyclic formals, which may, for example, take place by extraction with a suitable extraction agent or by distillation. Enrichment processes of this type are, for example, described in German Auslegeschrift No. 1,178,082 and British Patent No. 1,012,372. Other known enrichment processes may also find application for this purpose; reference may be made, for example, to Process Program, Stanford Institute Report 23 (1967), page 181 or to German Offenlegungsschrift No. 1,570,335. The refinement possibly required of the trioxane and of the cyclic formals optionally produced at the same time may also take place by known distillation and crystallization methods.

The process according to the invention is also particularly advantageous for process engineering reasons since the reaction can be carried out in simple equipment and short residence times can be employed. The formation of deposits and of by-products is, according to the invention, very small even with high formaldehyde concentrations.

The following examples are intended to explain the invention in more detail.

EXAMPLES

The trimerization of formaldehyde to form trioxane was carried out in a conventional tubular reactor. It consisted of a preheating zone and the actual reaction chamber in the form of a catalyst bed whose volume was 0.167 liter. An ion exchanger based on crosslinked polystyrene containing sulfonic acid groups with an exchange capacity of approx. 0.8 eq/liter (commercial product "Lewatit" made by BAYER AG) was used as catalyst. The formaldehyde solution was conveyed through the reactor by means of a pump; the residence time in the reactor was controlled by means of the pump output. The reaction temperature in the catalyst was recorded by means of a temperature sensing device and the system pressure was adjusted by means of an overflow valve. The reaction mixture in the receiving vessel was analyzed. Further details relating to the reaction conditions and to the results are listed in Table 1 below. This also contains the corresponding data of the comparison experiments.

Very similar results were obtained using a catalyst based on polytetrafluoroethylene containing sulfonic acid groups with an exchange capacity of approx. 1.2 eq/liter (commercial product "Nafion" made by Dupont).

From table 1 it can be seen that in comparison to the conventional synthesis method in circulation reactors with evaporators (Comparison Examples A and C) or in reactors with a column mounted on top (Comparison Example B), in the tubular reactor with a catalyst bed without the trioxane being distilled off (Examples 1–8) substantially smaller quantities of formic acid are obtained and that the ratio of the formic acid content and trioxane content is also substantially smaller. This means that the selectivity of the trioxane synthesis has been substantially improved. The trioxane contents obtained correspond to the equilibrium values of the reaction, at the same time the residence times according to the invention are substantially shorter than for the conventional process.

TABLE 1

Preparation of trioxane on solid bed catalysts

| Example | $W_{CH_2O}$ % of feedstock | Temperature (°C.) | Pressure (bar) | Residence time (min) | $W_{TOX}$ % of reaction mixture | $W_{HCOOH}$ % of reaction mixture | $\frac{W_{HCOOH} \times 100}{W_{TOX}}$ (= selectivity) | Paraformaldehyde deposition |
|---|---|---|---|---|---|---|---|---|
| 1 | 50 | 98 | 1 | 5.5 | 2.2 | 0.02 | 0.9 | — |
| 2 | 65 | 98 | 1 | 5.5 | 4.0 | 0.06 | 1.5 | — |
| 3 | 70 | 98 | 1 | 5.5 | 5.0 | 0.07 | 1.4 | — |
| 4 | 75 | 98 | 1 | 5.5 | 6.8 | 0.06 | 0.9 | — |
| 5 | 74 | 100 | 3 | 3.6 | 5.9 | 0.08 | 1.4 | — |
| 6 | 74 | 100 | 3 | 3.6 | 5.4 | 0.19 | 3.5 | — |
| 7 | 74 | 100 | 3 | 1.8 | 4.7 | 0.03 | 0.6 | — |
| 8 | 74 | 100 | 3 | 9.0 | 5.9 | 0.15 | 2.6 | — |
| Comparison Examples | | | | | | | | |
| A[1] | 65 | 100 | 1 | 60 | 3.5 | 0.32 | 9.1 | heavy |
| B[2] | 36.5 | 100 | 1 | 180 | | | 7.5* | not described |
| C[3] | 60 | 100 | 1 | 40 | | | 5.9 | not described |

\* $\frac{W_{HCOOH} \times 100}{W_{CH_2O converted}}$

[1]Experiment in a circulation reactor and evaporator according to European Patent 0,012,304
[2]Reactor with column mounted on it according to German Auslegeschrift 1,135,491 (experimental data taken from the publication)
[3]Example 4 of German Auslegeschrift 1,543,340 (experimental data taken from the publication)

We claim:

1. Process for the continuous preparation of trioxane, by trimerization of formaldehyde in aqueous solution, in the presence of acidic solid-bed catalysts, wherein the conversion is carried out without simultaneous evaporation.

2. A process as claimed in claim 1, wherein an ion exchanger based on a crosslinked polystyrene containing sulfonic acid groups is used as catalyst.

3. A process as claimed in claim 1, wherein an ion exchanger based on a fluoropolymer containing sulfonic acid groups is used as solid-bed catalyst.

4. A process as claimed in claim 1, wherein the residence times are between 2 and 5 minutes.

5. A process as claimed in claim 1, wherein the conversion takes place in a tubular reactor.

6. A process as claimed in claim 1, wherein the concentration of the formaldehyde solution is 60 to 80% by weight.

7. A process as claimed in claim 1, wherein cyclic formals are also prepared along with trioxane by trimerization of the formaldehyde in aqueous solution which contains in addition at least one diol or epoxide or a mixture comprising at least one diol and at least one epoxide.

8. A process as claimed in claim 1 wherein the conversion is effected under a temperature of from 80° to 140° C. and a pressure of from 0.5 to 10 bar.

9. A process as claimed in claim 8 wherein the temperature is between 90° and 120° C. and the pressure is between 1 and 5 bar.

* * * * *